United States Patent [19]

Nagata et al.

[11] Patent Number: 5,545,752
[45] Date of Patent: Aug. 13, 1996

[54] PROCESS FOR THE PREPARATION OF DIPHENYLAMINE OR NUCLEUS-SUBSTITUTED DERIVATIVE THEREOF

[75] Inventors: Teruyuki Nagata, Fukuoka-ken; Chiyuki Kusuda, Kumamoto-ken; Masaru Wada, Fukuoka-ken, all of Japan

[73] Assignee: Mitsui Toatsu Chemicals, Inc., Tokyo, Japan

[21] Appl. No.: 458,294

[22] Filed: Jun. 2, 1995

Related U.S. Application Data

[63] Continuation of Ser. No. 139,020, Oct. 21, 1993, abandoned.

[30] Foreign Application Priority Data

Oct. 28, 1992 [JP] Japan .................... 4-290132
Oct. 29, 1992 [JP] Japan .................... 4-291312

[51] Int. Cl.$^6$ ................................ C07C 209/18
[52] U.S. Cl. ............... 564/398; 564/433; 564/435
[58] Field of Search ..................... 564/398, 433, 564/435

[56] References Cited

U.S. PATENT DOCUMENTS

| | | | |
|---|---|---|---|
| 4,046,810 | 9/1977 | Moggi et al. | 260/571 |
| 4,124,639 | 11/1978 | Lutz et al. | 260/573 |
| 4,200,451 | 4/1980 | Vogel et al. | 71/118 |
| 4,804,783 | 2/1989 | Nagata et al. | 564/402 |
| 4,902,661 | 2/1990 | Immel et al. | 502/184 |
| 4,952,731 | 8/1990 | Nagata et al. | 564/402 |
| 5,117,063 | 5/1992 | Stern et al. | 564/398 |
| 5,196,592 | 3/1993 | Immel et al. | 564/415 |

FOREIGN PATENT DOCUMENTS

| | | |
|---|---|---|
| 494455 | 7/1992 | European Pat. Off. . |
| 2561238 | 3/1985 | France . |
| 49-14738 | 4/1974 | Japan . |
| 49-49924 | 5/1974 | Japan . |
| 57-58648 | 4/1982 | Japan . |
| 60-193949 | 10/1985 | Japan . |

OTHER PUBLICATIONS

DATABASE WPI, Week 8921, AN 89-156791, Apr. 18, 1989.
DATABASE WPI, Week 8639, AN 86-255392, Aug. 15, 1986.

*Primary Examiner*—Brian M. Burn
*Attorney, Agent, or Firm*—Burns, Doane, Swecker & Mathis

[57] ABSTRACT

A processes for the preparation of diphenylamine or a nucleus-substituted derivative thereof, which comprise, upon feeding into a reaction system a phenol compound and reacting in the reaction system a cyclohexanone compound with an aniline compound in the presence of a hydrogen transfer catalyst and a catalytic amount of the cyclohexanone compound corresponding to the phenol compound while using the phenol compound as a hydrogen acceptor and forming the cyclohexanone compound in the reaction system, (1) conducting reaction while adding dropwise the aniline compound and (2) employing a hydroxide, carbonate or bicarbonate of an alkali metal and/or alkaline earth metal when the hydrogen transfer catalyst is one of noble metals of Group VIII of the periodic table, respectively.

22 Claims, No Drawings

PROCESS FOR THE PREPARATION OF DIPHENYLAMINE OR NUCLEUS-SUBSTITUTED DERIVATIVE THEREOF

This application is a continuation of application Ser. No. 08/139,020, filed Oct. 21, 1993 (now abandoned).

BACKGROUND OF THE INVENTION

1. Field of the Invention

This invention relates to an improved process for the preparation of diphenylamine or a nucleus-substituted derivative thereof (hereinafter referred to as "diphenylamine and a derivative thereof" for the sake of brevity). More specifically, this invention relates to a process for the preparation of diphenylamine or a derivative thereof by using phenol or a nucleus-substituted derivative thereof (hereinafter referred to as "phenol or a derivative thereof" for the sake of brevity) as a hydrogen acceptor and reacting, in the presence of a hydrogen transfer catalyst, aniline or a nucleus-substituted derivative thereof (hereinafter referred to as "aniline or a derivative thereof") with cyclohexanone or a nucleus-substituted derivative thereof (hereinafter referred to as "cyclohexanone or a derivative thereof") corresponding to the phenol or the derivative thereof through condensation and inter-molecular hydrogen transfer. In particular, this invention is concerned with an industrially advantageous process for the preparation of diphenylamine or a derivative thereof by using a nucleus-substituted derivative of aniline as a raw material.

2. Description of the Related Art

Diphenylamine and derivatives thereof are useful compounds as intermediates for the production of dyes, agricultural chemicals, medicines, compounding agents for rubber and so on. For instance, 2-methyl-4-alkoxydiphenylamine, which can be obtained from a nucleus-substituted derivative of aniline, is highly valued for its usefulness as a raw material for fluoran dyes employed in pressure-sensitive or heat-sensitive recording papers.

Diphenylamine or a derivative thereof has heretofore been prepared by deammoniation of aniline or a derivative thereof; dehydration of a reaction product between aniline or a derivative thereof and phenol or a derivative thereof; or dehydrobromination of an reaction product between aniline or a derivative thereof and dibromobenzene.

Preparation of diphenylamine or a derivative thereof has also been proposed in patent publications, for example, in Japanese Patent Laid-Open Application No. 49924/1974 in which N-cyclohexylideneaniline is reacted in a vapor phase with an oxygen-containing gas in the presence of an oxidizing catalyst such as silica; in Japanese Patent Publication No. 14738/1974 in which phenol and aniline are reacted using γ-alumina as a catalyst; and in Japanese Patent Application Laid-Open No. 58648/1982 in which, upon preparing diphenylamine or a derivative thereof while reacting, in the presence of a hydroreduction catalyst, an amine and cyclohexanone or a derivative thereof to form a Schiff base, that is, an intermediate such as N-cyclohexylideneaniline, the synthesis is conducted using styrene or a derivative thereof as a hydrogen receptor.

These conventional processes are, however, accompanied by one or more drawbacks such as the need for complex reaction steps and/or low reaction velocity.

It is also disclosed in Japanese Patent Application Laid-Open No. 193949/1985 that diphenylamine or its derivative is prepared by reacting cyclohexanone or a derivative thereof with aniline or a derivative thereof in the presence of a hydrogen transfer catalyst while using phenol or a derivative thereof as a hydrogen acceptor and forming the cyclohexanone or the derivative thereof in a reaction system. This patent publication also discloses a process for obtaining 2-methyldiphenylamine in a yield of 97.0% (selectivity: 99.3%, conversion: 97.7%) by using 2-methylaniline and an excess amount of phenol in the presence of a palladium catalyst. This process is generally satisfactory from the viewpoints of the reaction velocity and selectivity. Industrial adoption of this process, however, is accompanied with the problems that phenol or a derivative thereof has to be used in large excess relative to aniline or a derivative thereof to suppress by production of N-cyclohexylaniline and the like and the expensive noble metal catalyst has to be added freshly in a large amount upon recovery and recycle of the catalyst.

SUMMARY OF THE INVENTION

An object of the present invention is to improve the process disclosed in Japanese Patent Application Laid-Open No. 193949/1985 and to provide an industrially advantageous process.

In one aspect of this invention, there is thus provided a process for the preparation of diphenylamine or a derivative thereof represented by the following formula (1):

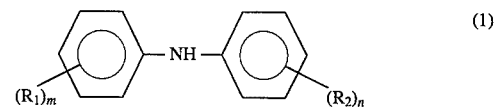

wherein $R_1$ is an alkyl or alkoxy group, m is an integer of 0 to 5, and where m is 2 or greater, the plural $R_1$s may be the same or different; and $R_2$ is an alkyl, alkoxy, carboxyl or an ester thereof, nitrile, aryl or hydroxyl group or a halogen atom, n is an integer of 0 to 5, and where n is 2 or greater, the plural $R_2$s may be the same or different, said process comprising:

(i) feeding into a reaction system phenol or a derivative thereof represented by the following formula (2):

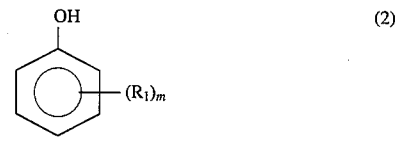

wherein $R_1$ and m have the same meanings as defined above; and reacting in the reaction system cyclohexanone or a derivative thereof represented by the following formula (3):

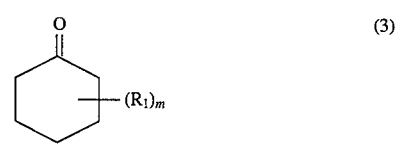

wherein $R_1$ and m have the same meanings as defined above with aniline or a derivative thereof represented by the following formula (4):

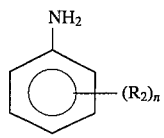

(4)

wherein $R_2$ and n have the same meanings as defined above in the presence of a hydrogen transfer catalyst and a catalytic amount of the cyclohexanone or the derivative thereof corresponding to the phenol or the derivative thereof while using the phenol or the derivative thereof as a hydrogen acceptor and forming the cyclohexanone or the derivative thereof in the reaction system, or (ii) converting, under hydrogen pressure in a reaction system, a portion of phenol or a derivative thereof of the formula (2) to a catalytic amount of the corresponding cyclohexanone or derivative thereof of the formula (3) without allowing the cyclohexanone or derivative of the formula (3) thereof to exist in the reaction system from the beginning of the reaction; and then reacting in the reaction system the cyclohexanone or the derivative thereof with aniline or a derivative thereof of the formula (4) while using the remaining portion of the phenol or the derivative thereof as a hydrogen acceptor and forming the cyclohexanone or the derivative thereof in the reaction system. The reaction is conducted while adding dropwise the aniline or the derivative thereof.

In a further aspect of this invention, there is also provided a process for the preparation of diphenylamine or a derivative thereof represented by the following formula (1):

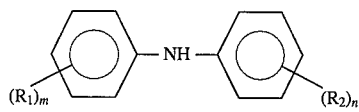

(1)

wherein $R_1$ is an alkyl or alkoxy group, m is an integer of 0 to 5, and where m is 2 or greater, the plural $R_1$s may be the same or different; and $R_2$ is an alkyl, alkoxy, carboxyl or an ester thereof, nitrile, aryl or hydroxyl group or a halogen atom, n is an integer of 0 to 5, and where n is 2 or greater, the plural $R_2$s may be the same or different, said process comprising:

(i) feeding into a reaction system phenol or a derivative thereof represented by the following formula (2):

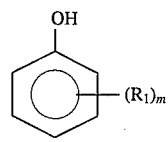

(2)

wherein $R_1$ and m have the same meanings as defined above; and reacting in the reaction system cyclohexanone or a derivative thereof represented by the following formula (3):

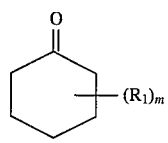

(3)

wherein $R_1$ and m have the same meanings as defined above with aniline or a derivative thereof represented by the following formula (4):

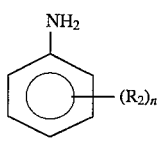

(4)

wherein $R_2$ and n have the same meanings as defined above in the presence of a catalyst of a noble metal of Group VIII of the periodic table and a catalytic amount of the cyclohexanone or the derivative thereof corresponding to the phenol or the derivative thereof while using the phenol or the derivative thereof as a hydrogen acceptor and forming the cyclohexanone or the nucleus-substituted derivative thereof in the reaction system, or (ii) converting under hydrogen pressure phenol or the derivative thereof of the formula (2) to a catalytic amount of the corresponding cyclohexanone or derivative thereof of the formula (3) without allowing the cyclohexanone or derivative thereof of the formula (3) to exist in the reaction system from the beginning of the reaction; and reacting in the reaction system the cyclohexanone or the derivative thereof of with aniline or its derivative represented of the formula (4) while using the phenol or the derivative thereof as a hydrogen acceptor and forming the cyclohexanone or the derivative thereof in the reaction system. The reaction is conducted by adding, as a cocatalyst, the hydroxide, carbonate or bicarbonate of an alkali metal and/or an alkaline earth metal.

According to the processes of the present invention, satisfactory results can be obtained from the viewpoints of the reaction velocity and the selectivity to the target product. According to the first process, by production of N-cyclohexylaniline is suppressed without using phenol or a derivative thereof in large excess relative to aniline or a derivative thereof. This permits a substantial reduction in the amount of phenol or a derivative thereof to be used, leading to the advantage that the volumetric efficiency is improved. According to the second process, when the used catalyst is used again after its recovery, the amount of the fresh catalyst to be added each time can be reduced substantially while maintaining the reaction velocity and yield at the same levels.

Combined use of the first and the second processes can of course bring about the advantages of both the processes.

The process in which diphenylamine or a derivative thereof is prepared by reacting aniline or a derivative thereof with phenol or a derivative thereof in the presence of cyclohexanone or a derivative thereof is extremely efficient, because the hydrogen formed as a result of dehydrogenation of the Schiff base, which is an intermediate obtained by the reaction between the aniline or the derivative thereof and the cyclohexanone or the derivative thereof, is fully utilized in the same reaction system for the reduction of the phenol or the derivative thereof, that is, for the formation of the cyclohexanone or the derivative thereof corresponding to the phenol or the derivative thereof. Some nucleus-substituted diphenylamines whose syntheses have heretofore been difficult as long as a single-stage process is used can still be used in one stage when one of the processes of the present invention is employed. Even if it is difficult to procure cyclohexanone or the corresponding derivative, the reaction can still be conducted provided that phenol or the corresponding derivative is available because the reaction can be performed by converting beforehand a portion of the phenol or the derivative thereof to cyclohexanone or the corresponding derivative thereof with hydrogen. Thus, these processes also have the advantage that they can be applied for the preparation of a wide range of diphenylamines.

DETAILED DESCRIPTION OF THE PREFERRED EMBODIMENTS

Phenols or its nucleus-substituted derivatives (which may hereinafter be referred to collectively as "phenol compound" for the sake of brevity) used as a hydrogen receptor in the processes of the present invention are represented by the following formula (2):

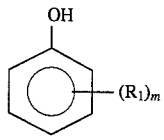
(2)

wherein $R_1$ is an alkyl or alkoxy group, for example, a methyl group, m is an integer of 0 to 5, for example, 0, 1 or 2, and where m is 2 or greater, the plural $R_1$s may be the same or different. Examples of the phenol compounds include phenol; alkylphenols such as methylphenol, ethylphenol, isopropylphenol, butylphenol, 2,4-dimethylphenol, 2,4,6-trimethylphenol, 2,6-di-t-butyl-4-methylphenol; and alkoxyphenols such as 3-methoxyphenol and 4-methoxyphenol. Among them, phenol is particularly preferred.

These phenol compounds are each converted by hydrogen to the corresponding cyclohexanone or derivative thereof which many hereinafter be referred to collectively as "cyclohexanone compound" for the sake of brevity. This hydrogen is formed as a result of dehydrogenation of a Schiff base, that is, an intermediate formed by the reaction between aniline or its derivative (which may hereinafter be referred to collectively as "aniline compound") and the cyclohexanone compound. To efficiently and completely use hydrogen formed in the reaction system, therefore, it is necessary to use the phenol compound in an amount equivalent to the aniline compound. To minimize the amount of by produced N-cyclohexylaniline or its derivative, it has heretofore been considered appropriate to use the phenol compound in an excess amount as much as 4–10 moles per mole of the aniline compound. According to the present invention, the aniline compound is added in the improved manner so that the target product can be obtained at high selectivity by using the phenol compound in an amount less than 2.0 moles per mole of the aniline compound.

Aniline or its nucleus-substituted derivative, namely, the aniline compound used in the processes of the present invention is represented by the following formula (4):

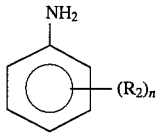
(4)

wherein $R_2$ is an alkyl, alkoxy, carboxyl or an ester thereof, nitrile, aryl or hydroxyl group or a halogen atom, for example, a methyl or methoxyl group or a chlorine atom, n is an integer of 0 to 5, for example, 1 or 2, and where n is 2 or greater, the plural $R_2$s may be the same or different. Illustrative aniline compounds include aniline; alkylanilines such as 2-methylaniline; dialkylanilines such as 3,4-dimethylaniline; alkoxyanilines such as 3-methoxyaniline; alkylalkoxyanilines such as 2-methyl-4-methoxyaniline; fluoroalkylanilines such as 2-fluoro-5-methylaniline; o-aminobenzoic acid and esters thereof, o-aminobenzonitrile, 4-benzylaniline and aminophenol. In particular, alkylanilines, alkoxyanilines, alkylalkoxyanilines can bring about high selectivity and are desirable aniline compounds.

When the reaction is conducted while adding dropwise the aniline compound, the amount of the phenol compound can be reduced and as mentioned above, the amount of the by product can also be suppressed.

The amount of dropwise addition per hour differs with the kind and quantity of the aniline compound, the reaction apparatus, the reaction temperature and the like, however, it may be adjusted to control the concentration of the Shiff base, that is, the intermediate in the reaction system at 20% or lower, preferably 10% or lower. If the concentration is greater than 20%, the amount of by produced N-cyclohexylideneaniline or the like tends to increase.

Cyclohexanone or its nucleus-substituted derivative, namely, the cyclohexanone compound used in the processes of the present invention is that corresponding to the phenol compound described above and is represented by the following formula (3):

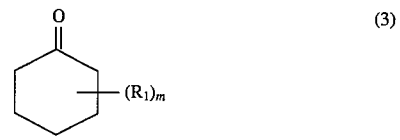
(3)

wherein $R_1$ is an alkyl or alkoxy group, for example, a methyl group, m is an integer of 0 to 5, for example, 0, 1 or 2, and where m is 2 or greater, the plural $R_1$s may be the same or different. These cyclohexanone compounds can be used in a catalytic amount of about 0.03 mole or more, preferably 0.05–0.40 mole per mole of the aniline compound. When the cyclohexanone compound is used in an amount smaller than 0.03 mole, the reaction velocity becomes lower. Amounts greater than 0.40 mole, on the other hand, may reduce the yield of the target diphenylamine compound. It is therefore not preferred to use the aniline compound in any amount outside the above range.

When the cyclohexanone compound is not allowed to exist in a catalytic amount from the beginning of the reaction, it is necessary to charge a reactor with hydrogen in an amount sufficient to form a suitable amount of the cyclohexanone compound from the phenol compound. Namely, hydrogen is charged in an amount of at least about 0.06 mole, preferably 0.10–0.80 mole per mole of the aniline compound while taking its conversion into consideration. After that, the reactants are heated and reacted.

The hydrogen transfer catalyst employed in the process of this invention is a dual-function catalyst which can promote both dehydrogenation and reduction. Ordinarily, a desired hydroreduction catalyst is also suited for dehydrogenation. Specific examples include Raney nickel, reduced-nickel- or nickel-carrying catalyst, Raney cobalt, reduced-cobalt- or cobalt-carrying catalyst, Raney copper, reduced-copper- or, copper-carrying catalyst and catalysts of noble metals of Group VIII of the periodic table.

Specific examples of the catalysts of the noble 10 metal of Group VIII of the periodic table include palladium catalysts such as palladium black, palladium oxide, colloidal palladium, palladium-carbon, palladium-barium sulfate and palladium-barium carbonate; platinum or platinum-carrying catalysts such as platinum black, colloidal platinum, platinum sponge, platinum oxide, platinum sulfide and platinum-carbon; rhodium catalysts such as colloidal rhodium, rhodium-carbon and rhodium oxide; and ruthenium catalysts.

Among these catalysts, palladium catalysts are preferred, with palladium-carrying catalysts such as palladium-carbon, palladium-alumina and palladium-magnesium oxide being particularly preferred. The catalyst may ordinarily be used in an amount of 0.001 to 0.2 gram-atom, preferably 0.004 to 0.1 gram-atom per gram-molecule of the aniline compound described above.

As cocatalysts usable in the present invention, the hydroxides, carbonates and bicarbonates of alkali metals and alkaline earth metals can be employed. Specific examples include lithium hydroxide, sodium hydroxide, potassium hydroxide, calcium hydroxide, magnesium hydroxide, sodium carbonate, potassium carbonate and sodium bicarbonate. Among them, sodium hydroxide and potassium hydroxide are preferred. These cocatalysts may be used either singly or in combination. The cocatalyst may be added to the reaction system independently from the catalyst of the noble metal of the VIII group of the periodic table. Alternatively, after a noble-metal-carrying catalyst is prepared, it is also possible to have an alkali metal and/or an alkaline earth metal component additionally carried from a solution of a salt, the hydroxide or the like of the alkali metal and/or alkaline earth metal and then to use the catalyst so prepared. The cocatalyst may be used in an amount of 2–30 wt.%, preferably 5–20 wt. % in terms of the alkali metal and/or alkaline earth metal component based on the catalyst metal. If the amount exceeds the upper limit, the reaction velocity tends to lower. If the amount is less than the lower limit, the yield is deteriorated.

The amount of the cocatalyst may be adjusted, as needed, by adding a fresh supply thereof together with a fresh supply of the catalyst of the noble metal of the VIII group of the periodic table, the latter fresh supply being added whenever the noble metal catalyst is recycled.

The reaction temperature is generally within a range of from 150° C. to 300° C., preferably from 170° C. to 280° C.

The diphenylamine or its derivative so formed can be obtained by treating the reaction mixture in a manner known per se in the art, for example, by distillation, crystallization, extraction or the like after the completion of the reaction. For example, after the completion of the reaction, the resulting reaction mixture is filtered to separate the catalyst. The catalyst so recovered can be used again. The filtrate is then concentrated, and the excess amount of the phenol compound is recovered with a cyclohexanone compound still contained therein. The distillate so collected is returned to the reaction system as it is, that is, in the form of the mixture. Diphenylamine or its derivative remaining in the vessel is then purified and isolated by distillation, crystallization or the like.

The present invention will hereinafter be described specifically by Examples.

EXAMPLE 1

A stainless steel autoclave whose internal capacity was 500 ml was charged with 28.3 g (0.3 mole) of phenol, 2.0 g (0.02 mole) of cyclohexanone and 1.07 g of 5% Pd/C (product of N.E. Chemcat Corporation). After a dropping funnel was charged with 21.4 g (0.2 mole) of 2-methylaniline and the autoclave was purged with nitrogen, the interior temperature of the autoclave was raised to 200° C. At the same temperature, 2-methylaniline in the dropping funnel was added dropwise to the resulting mixture under stirring over 5 hours. After completion of the dropwise addition, stirring was continued for a further one hour while maintaining the contents at the same temperature. The interior of the autoclave was then allowed to cool down to room temperature and then, the 5% Pd/C was filtered off from the reaction mixture. As a result of analysis of the filtrate by gas chromatography, it was found that the conversion of the 2-methylaniline was 99.6% and the selectivity to 2-methyldiphenylamine was 99.3%. N-Cyclohexyl-2-methylaniline was by produced in a yield of 0.6%.

EXAMPLES 2–5

In each Example, a reaction was carried out as in Example 1 except that the palladium catalyst, phenol, cyclohexanone and 2-methylaniline were used in the corresponding amounts shown in Table 1. The reaction mixture was then treated as in Example 1.

The results are presented in Table 1.

TABLE 1

| Example | 5% Pd/C (g) | Phenol (mole) | Cyclohexanone (mole) | 2-Methylaniline (mole) | Conversion (%) | Selectivity (%) | By production of N-cyclohexyl-2-methylaniline (%) |
| --- | --- | --- | --- | --- | --- | --- | --- |
| 2 | 1.07 | 0.24 | 0.02 | 0.2 | 99.4 | 98.5 | 1.2 |
| 3 | 1.07 | 0.38 | 0.02 | 0.2 | 99.9 | 99.6 | 0.3 |
| 4 | 1.07 | 0.30 | 0.08 | 0.2 | 100.0 | 99.7 | 0.3 |
| 5 | 1.07 | 0.30 | * | 0.2 | 99.8 | 99.5 | 0.5 |

*No cyclohexanone was charged. Hydrogen pressure was applied at 5 kg/cm$^2$G (0.15 mole per mole of 2-methylaniline).

EXAMPLE 6

A reaction was carried out as in Example 1 except that 2-methylaniline was added dropwise over 8 hours. The reaction mixture was treated as in Example 1. As a result, it was found that the conversion of 2-methylaniline was 99.4% and the selectivity to 2-methyldiphenylamine was 99.8%. N-Cyclohexyl-2-methylaniline was by produced in a yield of 0.1%.

Comparative Example 1

A stainless steel autoclave whose internal capacity was 300 ml was charged with 5% Pd/C, phenol, cyclohexanone and 2-methylaniline in the amounts as in Example 2. No dropping funnel was however employed. After the autoclave was purged with nitrogen, the temperature was raised to 200° C. After the resulting mixture was allowed to react for 5 hours under stirring while maintaining the temperature, the interior of the autoclave was allowed to cool down to room temperature and the 5% Pd/C was then filtered off from the reaction mixture. As a result of analysis of the filtrate by gas chromatography, it was found that the conversion of 2-methylaniline was 98.5% and the selectivity to 2-methyldiphenylamine was 91.8%. N-Cyclohexyl-2-methylaniline was by produced in a yield of 7.5%.

EXAMPLES 7–11

In each Example, a reaction was carried out as in Example 1 except that the corresponding phenol compound, cyclohexanone compound and/or aniline compound shown in Table 2 was employed instead of phenol, cyclohexanone and/or 2-methylaniline.

The results are presented in Table 2.

continued for a further one hour while maintaining the temperature. The autoclave was then allowed to cool down to room temperature. The reaction mixture was filtered to separate the 5% Pd/C. As a result of analysis of the filtrate by gas chromatography, it was found that the conversion of 2-methylaniline was 99.6% and the selectivity to 2-methyldiphenylamine was 99.3%.

TABLE 2

| Example | Phenol compound | Aniline compound | Target product | Conversion (%) | Selectivity (%) | By production of N-cyclohexyl-2-methylaniline- or its derivative (%) |
|---|---|---|---|---|---|---|
| 7 | 2,4-Dimethylphenol | 2-Methylaniline | 2,4,2'-Trimethyldiphenylamine | 95.6 | 98.7 | 0.7 |
| 8 | Phenol | 3,4-Dimethoxyaniline | 3,4-Dimethoxy-diphenylamine | 100.0 | 98.2 | 1.1 |
| 9 | Phenol | 2-Methyl-4-methoxyaniline | 2-Methyl-4-methoxy-diphenylamine | 99.7 | 99.0 | 0 6 |
| 10 | 2,4-dimethylpheno | 2-Methyl-4-methoxyaniline | 2-Methyl-4-methoxy-2',4'-dimethyl-diphenylamine | 99.5 | 97.8 | 1.0 |
| 11 | Phenol | 2-Fluoro-5-methylaniline | 2-Fluoro-5-methy-diphenylamine | 100.0 | 98.2 | 0.7 |

Note:
As the cyclohexanone compound in each Example, that corresponding to the phenol compound was employed.

EXAMPLE 12

A stainless steel autoclave whose internal capacity was 500 ml was charged with 53.5 g (0.5 mole) of 2-methylaniline, 235.3 g (2.5 moles) of phenol, 5.0 g (0.05 mol) of cyclohexanone, 2.68 g of 5% Pd/C (product of N.E. Chemcat Corp.) and 0.58 g of 1N-NaOH. After the autoclave was purged with nitrogen, the temperature was raised to 200° C. At the same temperature, the resulting mixture was allowed to react for 3 hours under stirring. The autoclave was then allowed to cool down to room temperature. The reaction mixture was filtered to separate the catalyst. A portion of the filtrate was sampled, followed by analysis by gas chromatography. As a result, it was found that the conversion of 2-methylaniline was 98.9% and the selectivity to 2-methyldiphenylamine was 99.2%.

The reaction was continued similarly using the catalyst recovered and adding 5% Pd/C and NaOH in the corresponding amounts as shown in Table 3. As a result, it was found that the amount of 5% Pd/C newly added in order to maintain the reaction velocity and selectivity was, on average, about 3% of the amount added at the beginning of the reaction.

EXAMPLE 13

A stainless steel autoclave whose internal capacity was 500 ml was charged with 141.2 g (1.5 mole) of phenol, 5.0 g (0.05 mole) of cyclohexanone, 2.68 g of 5% Pd/C (product of N.E. Chemcat Corp.) and 0.58 g of 1N-NaOH. After a dropping funnel was charged with 53.5 g (0.5 mole) of 2-methylaniline and the autoclave was purged with nitrogen, the temperature was raised to 200° C. At the same temperature, 2-methylaniline in the dropping funnel was added dropwise to the resulting mixture over 5 hours under stirring. After completion of the dropwise addition, stirring was continued for a further one hour while maintaining the temperature. The autoclave was then allowed to cool down to room temperature. The reaction mixture was filtered to separate the 5% Pd/C. As a result of analysis of the filtrate by gas chromatography, it was found that the conversion of 2-methylaniline was 99.6% and the selectivity to 2-methyldiphenylamine was 99.3%.

The reaction was continued further, while reusing the catalyst recovered and adding 5% Pd/C and NaOH in the corresponding amounts shown in Table 4. As a result, it was found that the amount of 5% Pd/C newly added in order to maintain the reaction velocity and the selectivity was, on average, about 1% of the amount added at the beginning of the reaction.

Comparative Example 2

A stainless steel autoclave whose internal capacity was 500 ml was charged with 53.5 g (0.5 mole) of 2-methylaniline, 235.3 g (2.5 moles) of phenol, 5.0 g (0.05 mole) of cyclohexanone and 2.68 g of 5% Pd/C (product of N.E. Chemcat Corp.). After the autoclave was purged with nitrogen, the temperature was raised to 200° C. At the same temperature, the resulting mixture was allowed to react for 3 hours under stirring. The autoclave was allowed to cool down to room temperature. The reaction mixture was then filtered to separate the catalyst. A portion of the filtrate was sampled and analyzed by gas chromatography. As a result, it was found that the conversion of 2-methylaniline was 98.6% and the selectivity to 2-methyldiphenylamine was 99.2%.

The reaction was continued further, while reusing the catalyst recovered and adding 5% Pd/C in the amount shown in Table 5. As a result, it was found that the amount of 5% Pd/C newly added in order to maintain the reaction velocity and the selectivity was, on average, about 5% of the amount added at the beginning of the reaction.

TABLE 3

| Re-cycling | Amount of catalyst newly added | | Conversion | Selectivity |
|---|---|---|---|---|
| | 5% Pd/C (g) | 1N-NaOH (g) | (%) | (%) |
| 1st | 0.08 | 0.35 | 98.4 | 99.3 |
| 2nd | 0.08 | 0.35 | 97.2 | 99.0 |
| 3rd | 0.03 | 0.35 | 96.6 | 98.8 |
| 4th | 0.13 | 0.35 | 98.8 | 99.2 |
| 5th | 0.08 | 0.35 | 97.5 | 98.7 |
| 6th | 0.08 | 0.35 | 96.7 | 97.9 |
| 7th | 0.13 | 0.35 | 98.5 | 98.8 |
| 8th | 0.08 | 0.35 | 96.2 | 97.6 |
| 9th | 0.08 | 0.35 | 98.0 | 99.0 |
| 10th | 0.08 | 0.35 | 96.5 | 98.0 |

TABLE 4

| Re-cycling | Amount of catalyst newly added | | Conversion | Selectivity |
|---|---|---|---|---|
| | 5% Pd/C (g) | 1N-NaOH (g) | (%) | (%) |
| 1st | 0.13 | 0.35 | 99.7 | 99.3 |
| 2nd | — | 0.35 | 99.8 | 99.2 |
| 3rd | — | 0.35 | 99.5 | 99.0 |
| 4th | — | 0.35 | 98.8 | 98.7 |
| 5th | — | 0.35 | 98.0 | 98.5 |
| 6th | — | 0.35 | 96.8 | 97.8 |
| 7th | 0.08 | 0.35 | 98.9 | 99.0 |
| 8th | — | 0.35 | 97.8 | 98.4 |
| 9th | 0.03 | 0.35 | 99.1 | 98.8 |
| 10th | 0.03 | 0.35 | 98.5 | 98.2 |

TABLE 5

| Re-cycling | Amount of catalyst newly added | | Conversion | Selectivity |
|---|---|---|---|---|
| | 5% Pd/C (g) | 1N-NaOH (g) | (%) | (%) |
| 1st | 0.08 | — | 99.6 | 98.9 |
| 2nd | 0.08 | — | 97.7 | 96.7 |
| 3rd | 0.27 | — | 99.5 | 98.3 |
| 4th | 0.13 | — | 99.1 | 97.0 |
| 5th | 0.13 | — | 98.9 | 96.7 |
| 6th | 0.13 | — | 97.9 | 95.8 |
| 7th | 0.27 | — | 98.9 | 97.9 |
| 8th | 0.08 | — | 97.5 | 97.5 |
| 9th | 0.08 | — | 97.2 | 96.9 |
| 10th | 0.13 | — | 96.3 | 96.7 |

What is claimed is:

1. In a process for the preparation of diphenylamine or a nucleus-substituted derivative thereof represented by the following formula (1):

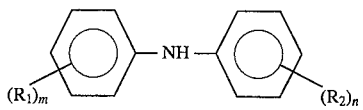
(1)

wherein $R_1$ is an alkyl or alkoxy group, m is an integer of 0 to 5, and where m is 2 or greater, the plural $R_1$s may be the same or different; and $R_2$ is an alkyl, alkoxy, carboxyl or an ester thereof, nitrile, aryl or hydroxyl group or a halogen atom, n is an integer of 0 to 5, and where n is 2 or greater, the plural $R_2$s may be the same or different, said process comprising:

feeding into a reaction system phenol or a nucleus-substituted derivative represented by the following formula (2):

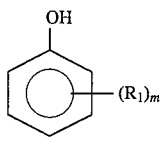
(2)

wherein $R^1$s and m have the same meanings as defined above and reacting in the reaction system cyclohexanone or a nucleus-substituted derivative thereof represented by the following formula (3):

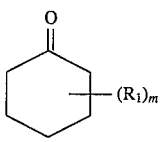
(3)

wherein $R_1$ and m have the same meanings as defined above with aniline or a nucleus-substituted derivative thereof represented by the following formula (4):

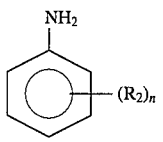
(4)

wherein $R_2$ and n have the same meanings as defined above in the presence of a hydrogen transfer catalyst and a catalytic amount of the cyclohexanone or the nucleus-substituted derivative thereof corresponding to phenol or the nucleus-substituted derivative thereof while using the phenol or the nucleus-substituted derivative thereof as a hydrogen acceptor and forming the cyclohexanone or the nucleus-substituted derivative thereof in the reaction system, the improvement wherein the reaction is conducted while adding dropwise the aniline or the nucleus-substituted derivative thereof so that the selectivity of the diphenylamine or nucleus-substituted diphenylamine is greater compared to the same process where aniline or the nucleus-substituted derivative thereof is added at one time.

2. A process of claim 1, wherein the reaction is conducted at 170°–280° C.

3. A process of claim 1, wherein the cyclohexanone or the nucleus-substituted derivative thereof present in the reaction system amounts to 0.05–0.4 mole per mole of the aniline or the nucleus-substituted derivative thereof.

4. A process of claim 1, wherein in the formula (2), $R_1$ is an alkyl or alkoxy group and m is 0 to 2.

5. A process of claim 1, wherein in the formula (4), $R_2$ is an alkyl or alkoxy group and n is 1 or 2.

6. In a process for the preparation of diphenylamine or a nucleus-substituted derivative thereof represented by the following formula (1):

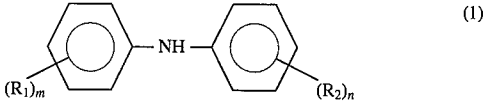
(1)

wherein $R_1$ is an alkyl or alkoxy group, m is an integer of 0 to 5, and where m is 2 or greater, the plural $R_1$s may be the same or different; and $R_2$ is an alkyl, alkoxy, carboxyl or an ester thereof, nitrile, aryl or hydroxyl group or a halogen atom, n is an integer of 0 to 5, and where n is 2 or greater, the plural $R_2$s may be the same or different, said process comprising:

converting, in the presence of a hydrogen transfer catalyst and under hydrogen pressure in a reaction system, a portion of phenol or a nucleus-substituted derivative represented by the following formula (2):

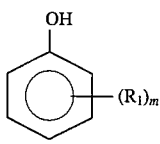
(2)

wherein $R_1$ and m have the same meanings as defined above to cyclohexanone or a nucleus-substituted derivative thereof represented by the following formula (3):

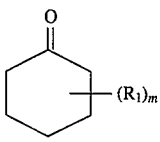
(3)

and reacting in the reaction system the cyclohexanone or the nucleus-substituted derivative thereof with aniline or a nucleus-substituted derivative thereof represented by the following formula (4):

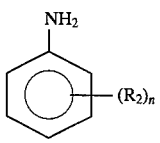
(4)

wherein $R_2$ and n have the same meanings as defined above while using the remaining portion of the phenol or the nucleus-substituted derivative thereof as a hydrogen acceptor and forming the cyclohexanone or the nucleus-substituted derivative thereof in the reaction system, the improvement wherein the reaction is conducted while adding dropwise the aniline or the nucleus-substituted derivative thereof so that the selectivity of the diphenylamine or nucleus-substituted diphenylamine is greater compared to the same process where aniline or the nucleus-substituted derivative thereof is added at one time.

7. A process of claim 6, wherein the reaction is conducted at 170°–280° C.

8. A process of claim 6, wherein the cyclohexanone or the nucleus-substituted derivative thereof present in the reaction system amounts to 0.05–0.4 mole per mole of the aniline or the nucleus-substituted derivative thereof.

9. A process of claim 6, wherein in the formula (2), $R_1$ is an alkyl or alkoxy group and m is 0 to 2.

10. A process of claim 6, wherein in the formula (4), $R_2$ is an alkyl or alkoxy group and n is 1 or 2.

11. In a batch process for the preparation of diphenylamine or a nucleus-substituted derivative thereof represented by the following formula (1):

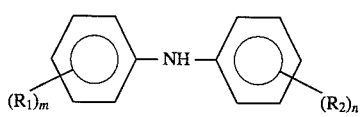
(1)

wherein $R_1$ is an alkyl or alkoxy group, m is an integer of 0 to 5, and where m is 2 or greater, the plural $R_1$s may be the same or different; and $R_2$ is an alkyl, alkoxy, carboxyl or an ester thereof, nitrile, aryl or hydroxyl group or a halogen atom, n is an integer of 0 to 5, and where n is 2 or greater, the plural $R_2$s may be the same or different, said process comprising:

feeding into a reaction system phenol or a nucleus-substituted derivative thereof represented by the following formula (2):

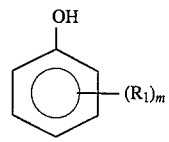
(2)

wherein $R_1$ and m have the same meanings as defined above, and reacting in the reaction system cyclohexanone or a nucleus-substituted derivative thereof represented by the following formula (3):

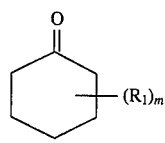
(3)

wherein $R_1$ and m have the same meanings as defined above with aniline or a nucleus-substituted derivative thereof represented by the following formula (4):

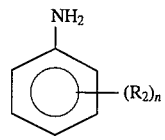
(4)

wherein $R_2$ and n have the same meanings as defined above in the presence of a catalyst of a noble metal of Group VIII of the periodic table and at least one cocatalyst selected from the group consisting of hydroxide, carbonate or bicarbonate of an alkali metal and/or an alkaline earth metal and a catalytic amount of the cyclohexanone or the nucleus-substituted derivative thereof corresponding to the phenol or the nucleus-substituted derivative thereof while using the phenol or the nucleus-substituted derivative thereof as a hydrogen acceptor and forming the cyclohexanone or the nucleus-substituted derivative thereof in the reaction system, the improvement wherein the catalyst is recovered and is used for a next batch of the reaction after adding new catalyst of the same noble metal of Group VIII of the periodic table and at least one cocatalyst selected from the group consisting of hydroxide, carbonate or bicarbonate of an alkali metal and/or an alkaline earth metal to the recovered catalyst wherein the amount of cocatalyst is about 2–30% by weight, in terms of the alkali metal and/or alkaline earth metal component based on the noble metal and wherein the amount of the new catalyst of the same noble metal of Group VIII is less than the amount of the new catalyst of the same noble metal of Group VIII in the absence of the addition of the cocatalyst to obtain the same selectivity of the diphenylamine or nucleus-substituted derivative thereof.

12. A process of claim 11, wherein the reaction is conducted at 170°–280° C.

13. A process of claim 11, wherein the cyclohexanone or the nucleus-substituted derivative thereof present in the reaction system amounts to 0.05–0.4 mole per mole of the aniline or the nucleus-substituted derivative thereof.

14. A process of claim 11, wherein in the formula (2), $R_1$ is an alkyl or alkoxy group and m is 0 to 2.

15. A process of claim 11, wherein in the formula (4), $R_2$ is an alkyl or alkoxy group and n is 1 or 2.

16. A process of claim 11, wherein the reaction is conducted while adding dropwise the aniline or the nucleus-substituted derivative thereof.

17. In a batch process for the preparation of diphenylamine or a nucleus-substituted derivative thereof represented by the following formula (1):

wherein $R^1$ is an alkyl or alkoxy group, m is an integer of 0 to 5, and where m is 2 or greater, the plural $R_1$s may be the same of different; and $R_2$ is an alkyl, alkoxy, carboxyl or an ester thereof, nitrile, aryl or hydroxyl group or a halogen atom, n is an integer of 0 to 5, and where n is 2 or greater, the plural $R_2$s may be the same or different, said process comprising:

converting, in the presence of a catalyst of a noble metal of Group VIII of the periodic table and at least one cocatalyst selected from the group consisting of hydroxide, carbonate or bicarbonate of an alkali metal and/or an alkaline earth metal under hydrogen pressure in a reaction system, a portion of phenol or a nucleus-substituted derivative thereof represented by the following formula (2):

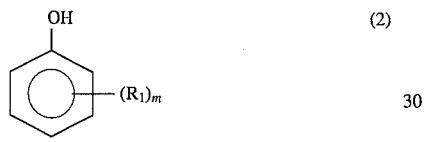

wherein $R_1$ and m have the same meanings as defined above to cyclohexanone or a nucleus-substituted derivative thereof represented by the following formula (3):

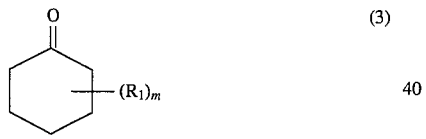

wherein $R_1$ and m have the same meanings as defined above and corresponding to the phenol or the nucleus-substituted derivative thereof and, while using the phenol or the nucleus-substituted derivative thereof as a hydrogen acceptor and forming the cyclohexanone or the nucleus-substituted derivative thereof in the reaction system, reacting the cyclohexanone or the nucleus-substituted derivative thereof with aniline or a nucleus-substituted derivative thereof represented by the following formula (4):

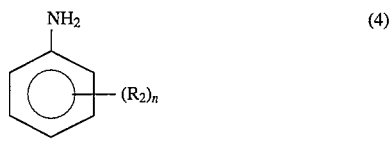

wherein $R_2$ and n have the same meanings as defined above, wherein the catalyst is recovered and is used for a next batch of the reaction after adding new catalyst of the same noble metal of Group VIII of the periodic table and at least one cocatalyst selected from the group consisting of hydroxide, carbonate or bicarbonate of an alkali metal and/or an alkaline earth metal to the recovered catalyst wherein the amount of cocatalyst is about 2–30% by weight, in terms of the alkali metal and/or alkaline earth metal component based on the noble metal and wherein the amount of the new catalyst of the same noble metal of Group VIII is less than the amount of the new catalyst of the same noble metal of Group VIII in the absence of the addition of the cocatalyst to obtain the same selectivity of the diphenylamine or nucleus-substituted derivative thereof.

18. A process of claim 17, wherein the reaction is conducted at 170°–280° C.

19. A process of claim 17, wherein the cyclohexanone or the nucleus-substituted derivative thereof present in the reaction system amounts to 0.05–0.4 mole per mole of the aniline or the nucleus-substituted derivative thereof.

20. A process of claim 17, wherein in the formula (2), $R_1$ is an alkyl or alkoxy group and m is 0 to 2.

21. A process of claim 17, wherein in the formula (4), $R_2$ is an alkyl or alkoxy group and n is 1 or 2.

22. A process of claim 17, wherein the reaction is conducted while adding dropwise aniline or the nucleus-substituted derivative thereof.

\* \* \* \* \*